US012702490B2

(12) United States Patent
Naudi et al.

(10) Patent No.: US 12,702,490 B2
(45) Date of Patent: Aug. 11, 2026

(54) METHOD FOR IMAGING AN IMPLANTED IMPLANT

(71) Applicants: BONETAG, Perpignan (FR); UNIVERSITÉ DE MONTPELLIER, Montpellier (FR); CENTRE NATIONAL DE LA RECHERCHE SCIENTIFIQUE, Paris (FR)

(72) Inventors: Stéphane Naudi, Perpignan (FR); Arnaud Vena, Saint-Mathieu-de-Tréviers (FR); Sylvain Dutrieux, Le Triadou (FR); Brice Sorli, Montagnac (FR)

(73) Assignees: BONETAG, Perpignan (FR); UNIVERSITE DE MONTPELLIER, Montpellier (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 167 days.

(21) Appl. No.: 18/549,125

(22) PCT Filed: Feb. 16, 2022

(86) PCT No.: PCT/EP2022/053752
§ 371 (c)(1),
(2) Date: Sep. 5, 2023

(87) PCT Pub. No.: WO2022/189106
PCT Pub. Date: Sep. 15, 2022

(65) Prior Publication Data

US 2024/0156546 A1 May 16, 2024

(30) Foreign Application Priority Data

Mar. 8, 2021 (FR) ...................................... 2102213

(51) Int. Cl.
*A61B 5/05* (2021.01)
*A61B 34/20* (2016.01)
(Continued)

(52) U.S. Cl.
CPC .............. *A61B 34/20* (2016.02); *G06T 17/00* (2013.01); *G06T 19/003* (2013.01); *G16H 50/20* (2018.01);
(Continued)

(58) Field of Classification Search
CPC ............ A61B 34/20; A61B 2034/2048; A61B 2034/2059
See application file for complete search history.

(56) References Cited

U.S. PATENT DOCUMENTS

| | | | |
|---|---|---|---|
| 2006/0016452 | A1 | 1/2006 | Goetz et al. |
| 2007/0238984 | A1 | 10/2007 | Maschke et al. |

(Continued)

FOREIGN PATENT DOCUMENTS

| | | | |
|---|---|---|---|
| CN | 103528495 | A | 1/2014 |
| CN | 111407279 | A | 7/2020 |
| WO | 2007/130510 | A2 | 11/2007 |

OTHER PUBLICATIONS

International Search Report and Written Opinion received for PCT/EP2022/053752, mailed May 20, 2022.

(Continued)

*Primary Examiner* — Joel F Brutus
(74) *Attorney, Agent, or Firm* — Greer, Burns & Crain, Ltd

(57) ABSTRACT

An imaging method and device configured to provide an image of an implant previously stored in a database, taking into account an arrangement of an implant implanted in a body is disclosed. To this end, a sensor such as a proximity sensor disposed outside the body is configured to detect a
(Continued)

portion of the implant in order to determine data relating to the positioning of same within the body.

15 Claims, 3 Drawing Sheets

(51) Int. Cl.

| | |
|---|---|
| ***G06T 17/00*** | (2006.01) |
| ***G06T 19/00*** | (2011.01) |
| ***G16H 50/20*** | (2018.01) |

(52) U.S. Cl.
CPC ................. *A61B 2034/2048* (2016.02); *A61B 2034/2059* (2016.02)

(56) References Cited

U.S. PATENT DOCUMENTS

| | | | | |
|---|---|---|---|---|
| 2008/0089566 | A1* | 4/2008 | Node-Langlois | G06T 7/30 382/128 |
| 2008/0294258 | A1* | 11/2008 | Revie | A61B 5/6878 623/18.11 |
| 2014/0187915 | A1* | 7/2014 | Yaroshenko | A61B 34/20 600/424 |
| 2015/0196365 | A1* | 7/2015 | Kostrzewski | A61B 90/39 606/130 |
| 2016/0278865 | A1* | 9/2016 | Capote | A61B 46/00 |
| 2016/0302692 | A1 | 10/2016 | Demmer | |
| 2017/0161434 | A1 | 6/2017 | Naudi | |
| 2017/0231709 | A1* | 8/2017 | Gupta | A61B 5/4566 600/424 |
| 2019/0183451 | A1* | 6/2019 | Yu | G06F 16/50 |
| 2019/0254754 | A1* | 8/2019 | Johnson | G06T 19/006 |
| 2020/0054215 | A1* | 2/2020 | Roche | A61B 5/4504 |
| 2020/0197103 | A1* | 6/2020 | Dees, Jr. | A61F 2/30942 |

OTHER PUBLICATIONS

French Search Report received for Application No. 2102213, dated Nov. 17, 2021.

Trobec, R., et al., “Metal implant localizers: frontiers and diagnostic feasibility,” Journal of Medical Engineering, vol. 20, No. 3, May/Jun. 1996, pp. 134-140.

* cited by examiner

METHOD FOR IMAGING AN IMPLANTED IMPLANT

BACKGROUND

The present invention relates to an imaging method of an implant, preferably comprising at least one metal part, implanted in a body, in particular a living being. It also relates to an imaging device implementing this imaging method.

The field of the invention is that of imaging methods and devices in the medical field, for example those which make it possible to evaluate the quality of placement and the correct operation of an implant and/or a prosthesis implanted in a body.

Methods are known for imaging elements implanted in the human body. These devices are functional but pose various problems, in particular:

- difficult to implement, as these processes use bulky devices and often require the use of a mobile imaging device to image the entire area of interest,
- safety, as they require the use of X-ray imaging which can be restrictive, as it involves paying attention to the X-ray dose used to image the living being,
- time, as such processes require the acquisition of a plurality of images in time and space in order to image the entire area of interest, and
- cost, because such processes are expensive, and this is often linked to the resources used to implement them, and the constraints they entail, such as the time required for computing and implementation.

One aim of the invention is to solve at least one of the above-mentioned shortcomings.

Another aim of the invention is to propose an imaging method for an implant implanted in a body that is easier to implement.

A further aim of the invention is to propose a safer imaging device.

A further aim of the invention is to propose a faster imaging device.

A further aim of the invention is to propose a less expensive imaging device.

SUMMARY

The invention makes it possible to achieve at least one of the aforementioned aims by an imaging method for an implant implanted in a body, comprising at least one iteration of a characterization phase comprising the following steps:

- measurement, by at least one sensor, known as the measurement sensor, located outside said body, supplying at least one electrical signal, known as the measured signal, relating to said implant,
- determination, by a processing unit, of at least one item of data relating to the positioning of said implant as a function of said measured signal and of a previously established model linking the at least one measured signal to the at least item of data relating to positioning, and
- provision, by a processing unit, of an image, referred to as measured, from at least one item of positioning data and a visual model relating to said implant.

Such a method is implemented using one or more measurement sensors and a processing unit, which denotes its ease of implementation.

The method according to the invention is also easy and faster to implement because it does not require taking an image of the actual implant implanted in the body, but of electrical signals relating to the implant, which is simpler to carry out and to process compared to capturing the image. Furthermore, as it uses a measured signal, and a visual model relating to said already-stored implant, said imaging method limits the computing time needed to provide the measured image and the implementation costs associated with these computing times.

In other words, once the implant is implanted in the body, the measured image that is provided by the method is a visual image either of this implant or another analogous implant that has been previously stored in a database. Said measurement step is in fact implemented not to produce this measured image as such but to determine a positioning of the implant in order to adapt the visual model previously established according to the actual disposition of the implant in the body.

The method according to the invention is also more secure because it is based on a measurement requiring no X-rays, which gives it simplicity of use and makes it safer and less harmful to the health of the body in which the implant is implanted.

The method according to the invention does not require the combination of a plurality of images to display the measured image. Therefore, the device according to the invention is faster.

As the method is simpler to implement, safer and faster, the associated costs are therefore less expensive.

The at least one item of data relating to positioning may comprise at least one item of position data and/or at least one item of inclination data and/or at least one item of orientation data and/or at least one state (folded and/or elongated) of said implant.

Preferably, the at least one item of data relating to positioning may comprise three position data and three orientation data of said implant.

If the implant is in a plurality of parts or comprises a plurality of parts, the at least one item of positioning data may comprise three position data and three orientation data, for example three spatial positions and three angles of inclination, for each part of the implant.

The step of provision may comprise a step of modifying the visual model relating to said implant from the at least one item of positioning data, such as for example a change in orientation of the visual model or of part of the visual model.

The measuring step may measure at least one magnetic signal to provide the at least one measured signal.

The visual model may be a real image of said implant, that is an image from which the actual dimensions of the implant can be extracted.

The visual model may be a prerecorded image of said implant, for example an image provided by the manufacturer of said implant. In another variant, the visual model may be generated by scanner imaging.

The term “body” refers to the body of an object, or a robot, or a living being such as an animal or a human.

The imaged implant can be a unitary implant, such as for example a femoral or tibial implant.

The imaged implant may consist of a plurality of parts, for example a hip or shoulder implant wherein two parts engage, or an ankle implant composed of three parts.

Alternatively, the implant may comprise at least two parts, at least one of which is movable relative to the rest of the implant, such as for example a knee implant composed, for example, of a femoral and tibial implant, an elbow implant, etc.

The visual model relating to said implant can be a three-dimensional image of said implant.

The measured image may be a three-dimensional image.

Thus, the method according to the invention can provide a three-dimensional image of said implant while being easy to implement, fast, safe and less expensive.

The measuring step of the method according to the invention may comprise a measurement, by at least one inertial sensor, of at least one item of inertial data relating to the body, and in that the step of providing the measured image comprises an adjustment of the orientation of the visual model.

The measurement of the inertial data makes it possible to position said implant in space, in particular to assign it to at least one orientation, for example an exact angle of inclination as it is found during the measurement step in the body in which it is implanted.

The method according to the invention can compute from the inertial data:

- the position and orientation, for example at least one angle of inclination, preferably three angles, in the three-dimensional space of the implant, and/or
- the position and orientation, for example at least one angle of inclination, preferably three angles, of the implant relative to a chosen reference frame, for example the floor.

The method according to the invention can by this measurement know the relative movement of the part of the body comprising the implant, relative to a chosen reference frame, for example the floor. The method according to the invention can therefore determine whether the patient is lying down or standing during the examination and also reconstruct a lateralized measured image, that is one capable of giving a right or left view of the part of the body comprising the implant.

The method according to the invention may comprise a plurality of iterations of the characterization phase each providing a measured image, said method further comprising generating a video from said measured images.

The method according to the invention thus makes it possible to generate a video image of the implant and therefore to reconstruct the dynamics of a movement of a part of the body in which the implant is implanted. Dynamic imaging of said implant can therefore be stored.

Such a video makes it possible to track the movements of the implant and in particular of the various parts of the implant when the implant comprises parts in motion relative to one another.

The at least one measured signal may comprise:

- an electrical impedance, known as individual or independent impedance, for each measurement sensor, or
- an electrical impedance, known as mutual impedance, for each measurement sensor coupled to at least one other measurement sensor, or
- an electrical voltage.

The measurement sensors used to measure the measured signals may be derived from components available on the market or conversely, to be fully customized, for example from copper conductors.

The measurement sensor can be arranged to measure at least one magnetic signal and provide, at the output, the at least one measured signal. The signal at the output of the measurement sensor can be proportional to the signal at the input of the measurement sensor.

The visual model of said implant can be stored in a database.

For at least one implant, the visual model relating to said implant can be stored in association with an identifier of the implant. In this case, the method according to the invention may comprise a step of identifying the implant in order to retrieve said visual model relating to said implant.

The implant implanted in the body can be identified by the patient or the person in the body of which the implant is implanted, by providing an item of identification data for the implant.

Alternatively, the method according to the invention may comprise a step of identifying the implant by reading an item of identification data provided by said implant.

For example, the identification step may comprise a step of reading an item of identification data stored in an electronic device integrated into the implant. Such an electronic device may comprise a radio tag comprising an antenna associated with an electronic chip containing at least one item of identification data of the implant, and optionally complementary data.

The identification data stored in such an electronic device can be read by an electronic reader. The electronic reader can be external to said implant.

The reading of the implant identification data may be similar to that described in French patent 3 017 227 A1.

According to yet another alternative, the visual model relating to said implant can be retrieved directly from the patient, which allows the method according to the invention to be implemented by any practitioner who has the elements making it possible to implement said method.

The visual model of the method according to the invention can be stored in a database, said method being able to comprise a step of exchanging data between said processing unit and said database to perform the step of provision.

The method according to the invention can also retrieve the visual model from a database.

Any database mentioned may be local, by being stored on a local server, or external by being stored on an external server. The database can be connected with the processing unit of the method according to the invention.

The connection with this local or external server can be wired, or wireless via an Internet connection such as WIFI, cellular network, mobile telephony or GSM, for example the 4G or 5G network. It can be done by a network and/or Internet connection. The local or external server may be able to communicate with the processing unit used in the method according to the invention.

The method according to the invention may comprise searching a database of the visual model based on the implant identification data.

The implant identification data can be determined from the patient's medical records. The patient records can be found by a specialist in charge of the person comprising the implant and/or from the patient records saved locally or on a network database.

The identification data of the implant can make it possible to retrieve other information, for example the manufacturer, the model of the implant and its dimensions.

Thus, in the method according to the invention, the exact geometry of the implant is known beforehand. The exact geometry of the implant can therefore be obtained from the patient's medical records stored in a database or from the electronic device combined with the radio tag reader.

The method according to the invention may comprise, prior to the first iteration of the characterization phase, a preliminary phase carried out when said implant is outside said body, said preliminary phase comprising at least one iteration of the following steps of:

- measurement, by at least one sensor, known as the measurement sensor, located outside said body, supplying at least one electrical signal, known as the reference signal, and
- storage of the at least one reference signal in association with at least one item of positioning data, referred to as an item of reference positioning data, of said implant.

Thus, according to the method according to the invention, each measured reference signal is associated with at least one item of reference positioning data of said implant.

The prior phase makes it possible to record positions of said implant that will be implanted in order to know the orientations, inclinations, positions, and exact states of said implant in relation to at least one reference signal. The term exact state is understood to mean, for example, a folded or elongated state of said implant.

The prior phase can then be used by the processing unit in the determination step in order to determine the at least one item of data relating to the positioning of said implant implanted in said body. In this case, the item of reference positioning data can be associated with the at least one item of positioning data used by the processing unit in the step of providing the measured image.

The at least one measurement sensor used in the prior phase may be similar to, identical, or different from the at least one measurement sensor used during the measurement step.

The at least one item of reference positioning data of said implant comprises at least one item of inclination data and/or at least one item of positioning data.

Preferably, the reference signal can be stored in the storage step with three items of inclination data and three items of positioning data relating to said implant.

Preferably, the implant is positioned on a mobile support in the prior phase. The mobile support comprises at least one degree of freedom in rotation, and/or in translation. This makes it possible to record various items of implant positioning data associated with at least one reference signal.

Preferably, the mobile support of said implant comprises three rotational degrees of freedom and three translational degrees of freedom.

In this way, all the positions and orientations of the implant can be recorded. The data recorded in the prior phase is accurate and complete.

The implant is preferably imaged from all of its viewing angles.

The previously established model can comprise:

- a supervised neural network trained with a database and taking as input the at least one measured signal, said database linking a measured signal with an item of positioning data, or
- a pre-recorded table, for example a chart, associating at least one electrical signal with at least one item of data relating to the positioning of said implant, or
- a mathematical relationship between the at least one measured signal and the at least one item of positioning data.

The training of the neural network can be carried out with data previously recorded in the prior phase, for example those recorded in the database following the storage step. For example, the training can be carried out from 100 reference signals associated with three position data and three reference inclination data and 20 unknown measured signals, that is, not associated with at least one item of positioning data. Of course, the supervised neural network can be tested with test data, for example 20 unknown measured signals.

The table can be recorded in the prior step of said method. In this case the processing unit can be arranged to compute the correlation between the electrical signals recorded in the table and those measured in the measurement step. The processing unit can be arranged to select the at least one item of position data associated with the electrical signal of the table having the strongest correlation with the at least one measured signal.

The mathematical relationship may be an array or a transfer function connecting the at least one measured signal to the at least one item of positioning data.

According to another aspect of the invention, a device for imaging an implant implanted in a body is proposed, comprising means configured to implement the imaging method according to the invention.

In particular, said imaging device according to the invention can comprise:

- at least one sensor, known as the measurement sensor, located outside said body and arranged to supply at least one electrical signal, known as the measured signal, relating to said implant,
- a processing unit arranged to:
  - determine at least one item of data relating to the positioning of said implant as a function of the measured signal and of a previously established model linking the at least one measured signal to the at least item of data relating to positioning, and
  - provide an image, referred to as the measured image, from at least one item of positioning data and a visual model relating to said implant.

The at least one sensor may preferably be arranged to measure at least one magnetic signal and provide at least one electrical signal.

The imaging device according to the invention requires using one or more measurement sensors and a processing unit, which denotes its ease of implementation.

The device according to the invention does not require using an X-ray imaging system, which makes it simpler to implement, safer, and less expensive.

In general, the imaging device according to the invention makes it possible to obtain advantages similar to those developed for the imaging method according to the invention since it is arranged to implement it.

The at least one measurement sensor may preferably be an inductive sensor.

The processing unit may comprise a first computing module configured to determine the at least one item of positioning data as a function of the at least one measured signal and the previously established model.

The processing unit may comprise a second computing module to provide the measured image as a function of the at least one item of positioning data and of the visual model of the implant. Optionally, the second module can take into account the inertial data in order to adjust the orientation of said visual model.

The processing unit may comprise a communication module for exchanging data with a database.

The imaging device according to the invention may comprise at least one inertial sensor arranged to measure at least one item of inertial data relating to the body, said inertial data being able to be used by the processing unit to adjust the orientation of the visual model.

At least one inertial sensor may comprise a contact sensor in contact with a surface of said body.

Thus, the device according to the invention can know the relative movement of the part of the body comprising the implant in the space with respect to a chosen reference frame, such as the floor.

The at least one measurement sensor carrying out the measurement of said measured signal may comprise, or be, a near field sensor.

The at least one electrical sensor can be inductive.

Thus, the imaging device according to the invention can use measurement sensors without contact with said body.

The at least one measurement sensor may comprise a proximity sensor, preferably detecting conductive materials (e.g., metal), or magnetic materials.

The at least one measurement sensor of the device according to the invention may comprise a contactless sensor.

The at least one measurement and/or inertial sensor can be movable.

The imaging device according to the invention may comprise multiple measurement sensors forming an array of sensors, said array being arranged to surround at least part of the body comprising said implant.

Thus, the device according to the invention may comprise multiple measurement sensors measuring the measured signal. These measurement sensors are arranged in an arrangement that allows them to surround the area of the body comprising the implant (area of interest). A map of the area can be obtained by such an arrangement. The measurement of the measured signal is therefore carried out according to a multitude of capture angles. Such an arrangement of the measurement sensors makes it possible to precisely determine the position of one or more implants or particular areas of the implant.

The device according to the invention may comprise a measurement sensor used as a receiver. For example, the implant can be arranged to send at least one signal that can then be received by the measurement sensor used as a receiver. In another variant device according to the invention, the measurement sensor used as a receiver can receive a signal reflected by the implant.

The device according to the invention may comprise multiple measurement sensors comprising at least one measurement sensor used as a receiver and a measurement sensor used as a transmitter. For example, one of the measurement sensors used as a transmitter can be arranged to send a signal to the implant. This signal may preferably be magnetic. On receiving the signal, the implant can switch from a standby mode to an active mode and thus retransmit a signal that can be received by the measurement sensor used as a receiver.

The implant can therefore reflect part of the signal, preferably a part of the magnetic field, that is incident emitted by the at least one measurement sensor used as a transmitter. This reflected magnetic field can be received by a receiver measurement sensor.

In a variant, the sensor used as a receiver and the at least one sensor used as transmitter can be included in the same measurement sensor (that is the same assembly).

The measurement sensor used as a transmitter may comprise an inductor, for example a coil, arranged to send a signal, preferably being intended for the implant. The signal can be modified according to the position and/or orientation and/or movement of the implant.

The signal transmitted by the measurement sensor used as a transmitter may be an electrical, or preferably magnetic, signal, for example inductive, or electromagnetic.

The signal received by the measurement sensor used as a receiver may be an electrical, or preferably magnetic, signal, for example inductive, or electromagnetic.

The coupling between a plurality of measurement sensors may be, preferably, inductive or capacitive.

The at least one measurement sensor may comprise a part used as a receiver and a part used as a transmitter.

The imaging device according to the invention may comprise multiple measurement sensors forming a plurality of measurement sensor arrays arranged to surround at least part of the body comprising said implant, each array being able to comprise:

- a measurement sensor used as a transmitter, and
- a plurality of measurement sensors used as receivers and positioned on the measurement sensor used as a transmitter.

Such an arrangement makes it possible to improve the measurement precision of the measured signals since the measurement sensors are more sensitive to modifications in the field induced by the movements of the implant.

The measurement sensor used as a transmitter may be a loop and/or form a loop. The loop is preferably closed and/or circular in shape.

The measurement sensors used as receivers can be positioned on the entire perimeter of the measurement sensor used as a transmitter.

Each array of measurement sensors is arranged to provide a number n of measurements of the measured signal as a function of the number of measurement sensors used as receivers in said array.

The measurement sensors of each loop can be coupled to each other by mutual induction.

Each measurement sensor coupled to another measurement sensor in the array may be arranged to provide a measurement of the measured signal relating to said implant.

The measurement provided by each measurement sensor coupled to another measurement sensor may comprise a mutual inductance.

At least one measurement sensor measuring said measured signal can comprise:

- at least one capacitive sensor, and/or
- at least one inductive sensor.

Each inductive measurement sensor may comprise a coil.

The measurement sensor arrays may be similar or different in arrangement. For example, the device may comprise three arrays and therefore two similar ones and one comprising at least one measurement sensor more or less than the other two arrays.

The imaging device according to the invention may comprise at least one recording means arranged to acquire the at least one electrical signal.

The device according to the invention can therefore produce a video or sequences of images of the implant.

The at least one electrical signal measured by the sensor or the multiple measurement sensors can comprise:

- the electrical impedance of each measurement sensor, and/or
- the electrical impedance, known as mutual impedance, for each measurement sensor coupled to at least one other measurement sensor, and/or
- a voltage for each measurement sensor.

The value of the self-impedance and/or mutual impedance and/or voltage may be a function of an orientation of the at least one implant.

The processing unit can be arranged to compute from the self-impedance or mutual impedance or the voltage measured by the at least one sensor for measuring angles of rotation and/or a movement of said implant.

The imaging device according to the invention may comprise at least one electronic reader that can be arranged to read an item of identification data stored in an electronic device integrated into said implant in order to retrieve said visual model relating to said implant.

Such an electronic device may comprise a radio tag comprising an antenna associated with an electronic chip containing the item of identification data of the implant, and optionally complementary data.

The implant identification data may comprise the identifier of said implant.

The electronic device may comprise the visual model relating to said implant. Thus, the device according to the invention can be arranged to read the visual model included in said radio tag.

The radio tag may be an RFID device, for example a passive or active RFID. The radio tag may be a transponder, an RFID tag.

The electronic device may comprise at least one sensor arranged to record the complementary data.

The electronic device, and/or electronic reader and/or the processing unit according to the invention may be similar to those described in French patent application 3 017 227 A1, relating to a device for managing implant data, a system comprising this device and use of this system.

The visual model relating to said implant can be recorded on a database able to communicate with said device according to the invention.

Therefore, the visual model can be communicated by the electronic device or taken from, for example, the medical record of said implant (a record saved on a network, for example) saved in a database or a local or external server or any other storage means to which said device according to the invention is connected.

Said implant may comprise at least one location indicator.

The location indicator can be arranged to give at least one spatial reference point of said implant and/or portions or areas of said implant.

The location indicator may comprise at least one protrusion and/or notch in said implant.

The location indicator may comprise an insert composed of a material different from the implant. The material of the insert may be metallic, dielectric or magnetic.

The location indicator may comprise a resonator positioned on said implant arranged to amplify a magnetic and/or electrical field to the measurement sensor(s) measuring the measured signal.

The implant can be composed of or comprise metal.

The device and/or the method according to the invention can therefore be effective on implants that cannot be imaged with standard imaging techniques such as Magnetic Resonance Imaging (MRI) or scanners.

BRIEF DESCRIPTION OF THE DRAWINGS

Other benefits and features shall become evident upon examining the detailed description of entirely non-limiting embodiments and implementations, and from the following enclosed drawings.

DETAILED DESCRIPTION

In particular, all of the described variants and embodiments can be combined with each other if there is no technical obstacle to this combination.

In the figures, the same reference has been used for the features that are common to several figures.

Figure 1:
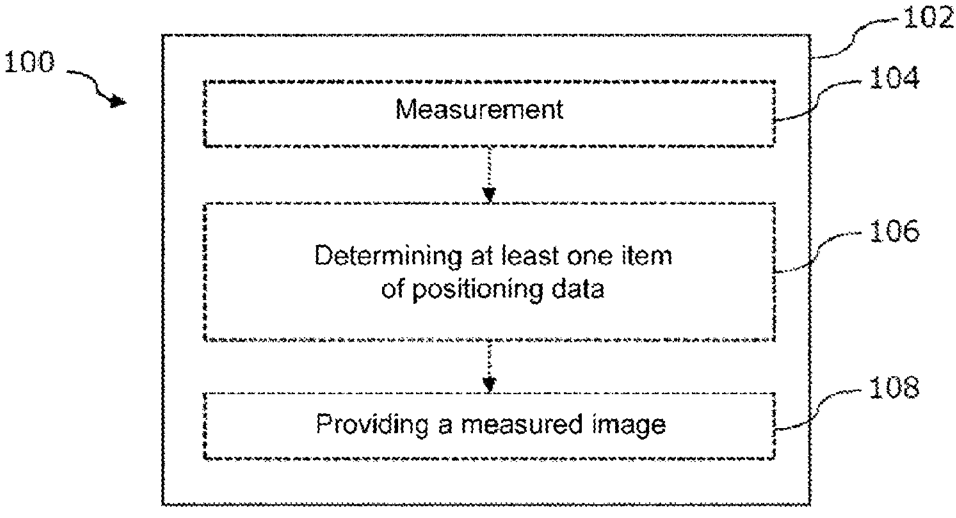
FIG. 1 is a schematic representation of a first non-limiting example embodiment of a method according to the invention.

FIG. 1 is a schematic representation of a first non-limiting example embodiment of a method 100 according to the invention.

The method 100 is computer-implemented.

The method 100 is a method 100 for imaging an implant implanted in a body, comprising at least one iteration of a characterization phase 102.

The characterization phase 102 comprises the following steps:

- measurement 104, by at least one sensor, known as the measurement sensor, located outside said body, supplying at least one electrical signal, known as the measured signal, relating to said implant,
- determination 106, by a processing unit, of at least one item of data relating to the positioning of said implant as a function of said measured signal and of a previously established model linking the at least one measured signal to the at least item of data relating to positioning, and
- provision 108, by a processing unit, of an image, referred to as measured, from at least one item of positioning data and a visual model relating to said implant.

Preferably, the measurement sensor is arranged to measure at least one magnetic field and provide, at the output of the measurement sensor, at least one electrical signal.

The visual model may be a scale image of said implant, for example an image provided by the manufacturer of said implant.

The previously established model can be a supervised neural network taking the at least one measured signal as input. The database can connect a measured signal with at least one item of positioning data.

In a first variant method 100, the visual model is a two-dimensional image. The measured image can thus be two-dimensional.

In a second variant method 100, the visual model is a three-dimensional image. In this case, the measured image can be three-dimensional or two-dimensional.

In a variant of the method 100, the measuring step 104 can comprise a measurement of an inertial data relating to the body. In this case, the step of generating the measured image may comprise an adjustment of the orientation of the visual model.

Each iteration of the characterization phase 102 provides a measured image.

The method 100 can perform multiple iterations of the characterization phase 102. In this way, multiple measured images are obtained. The method 100 may, from the plurality of measured images obtained, generate a video or sequence of images. Thus, the dynamic properties of the implant can be observed and/or studied.

Figure 2:
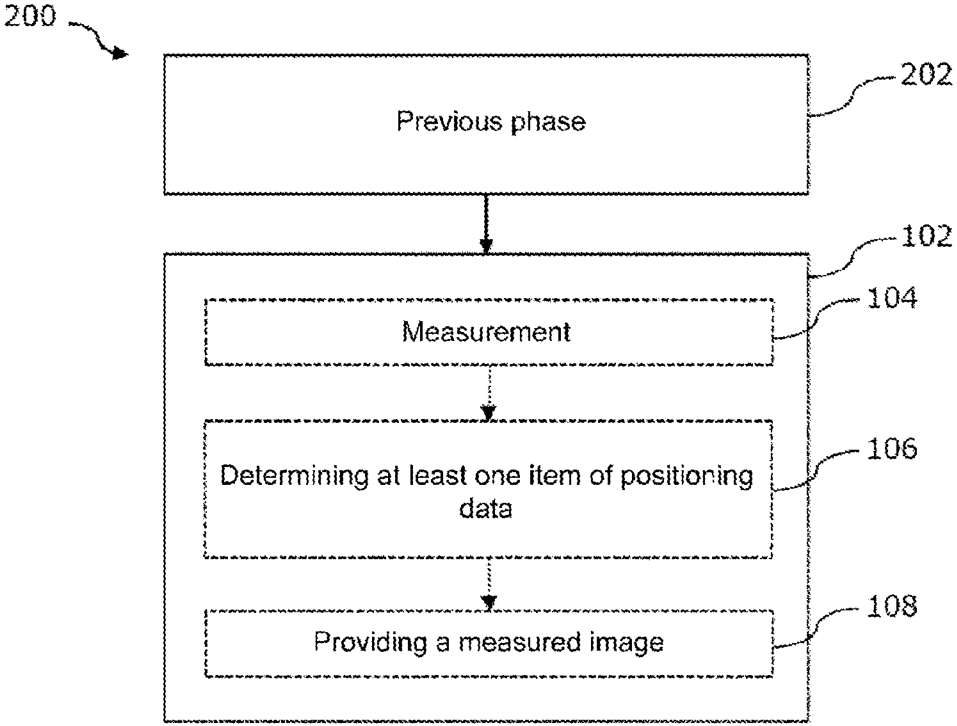
FIG. 2 is a schematic depiction of a second example embodiment of a method according to the invention.

FIG. 2 is a schematic depiction of a second example embodiment of a method 200 according to the invention.

The imaging method 200 comprises the same steps as the method 100 shown in FIG. 1.

The method 200 further comprises a preliminary phase 202. The preliminary phase 202 was carried out before the first iteration of the characterization phase 102. In particular, the preliminary phase 202 is carried out when said implant is outside said body.

The preliminary phase 202 comprises a step of measuring, by at least one sensor, called a measurement sensor, arranged outside said body, at least one electrical signal, called a reference signal.

The preliminary phase 202 also comprises a step of storing said at least one reference signal in association with at least one item of positioning data, referred to as reference positioning data, of said implant.

The memorization step can be carried out on a storage element such as a hard drive internal or external to the processing unit, a local or external database connected to the processing unit.

Preferably, during the preliminary phase 202, the implant is positioned on a movable support. The mobile support comprises three degrees of freedom in rotation, three degrees of freedom in translation. This makes it possible to record various data relating to the positioning of the implant, associated with at least one reference signal. The implant is preferably imaged from all of its viewing angles.

The at least one sensor for measuring the prior phase 202 is similar to that used for the measuring step 104.

Figure 3:
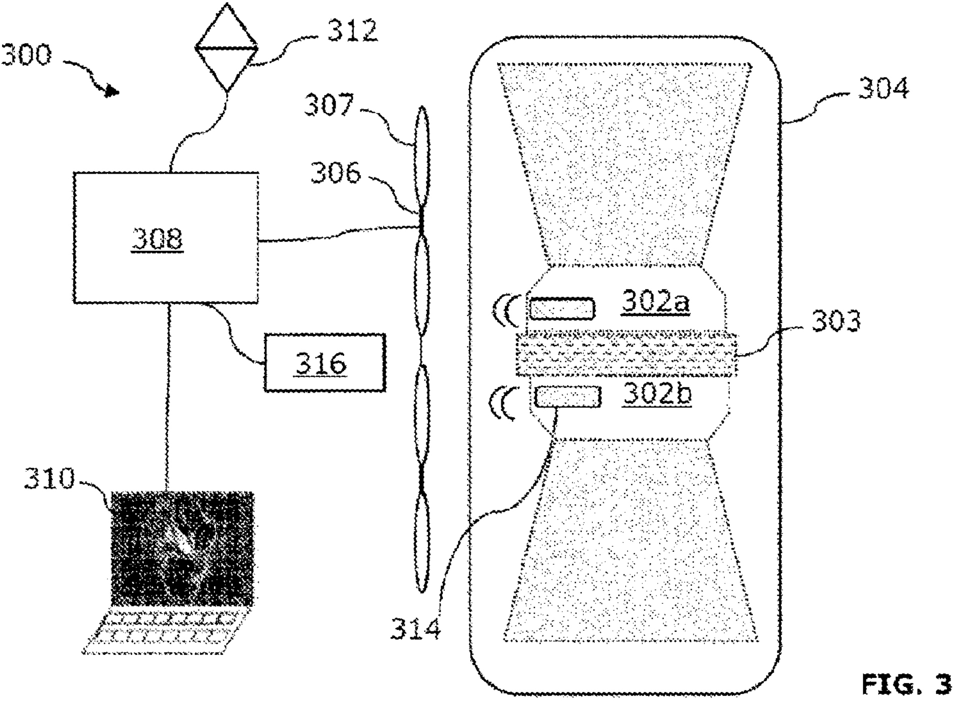
FIG. 3 is a schematic representation of a first non-limiting example embodiment of a device according to the invention.

FIG. 3 is a schematic depiction of a first example embodiment of a device 300 according to the invention.

The device 300 is an imaging device 300 of an implant 302 implanted in a body 304, arranged to implement, in a non-limiting manner, the imaging method 100 or 200 shown in FIGS. 1 and 2.

The device 300 comprises:

- at least one measurement sensor 306, located outside said body 304 and arranged to supply at least one measured signal relating to said implant 302,
- the processing unit 308 arranged to:
  - determine at least one item of data relating to the positioning of said implant 302 as a function of the measured signal and of the previously established model linking the at least one measured signal to the at least item of data relating to positioning,
  - provide the measured image 310, from at least one item of positioning data and the visual model relating to said implant 302.

The signal received by the measurement sensor 306 is preferably a magnetic field. The signal measured at the output of the measurement sensor 306 is preferably a voltage.

FIG. 3 shows an implant 302 implanted in a living being, in particular a human or a robot. In a non-limiting manner, the implant corresponds to a knee prosthesis, and comprises two parts 302*a* and 302*b*, a first part 302*a* of which corresponding to a femoral implant 302*a* and a second part 302*b* corresponding to a tibial implant 302*b*. The two parts 302*a* and 302*b* of the implant 302 are mobile relative to each other. The implant 302 shown in FIG. 3 also comprises an intermediate layer 303 positioned between the two parts 302*a* and 302*b* of the implant 302. Of course, the intermediate layer 303 as shown in FIG. 3 can adapt to all types of joint implants, such as sleds of knee prostheses, humeral cups of shoulder prostheses, acetabular cups of hip prostheses, etc.

Preferably, the implant 302 is made of metal or comprises metal. The implant 302 may also comprise other materials, for example plastic, and/or a polymer material. The intermediate layer may be made of polyethylene.

The processing unit 308 may be a computing means, such as a processor, a computer, arranged to execute a computer program or command lines dedicated to the step or the operation to be carried out.

The processing unit 308 may comprise multiple computing modules, in particular all the modules, that can be integrated into the same processor.

The device 300 comprises a measurement sensor 306 comprising multiple capture sites 307 to capture the at least one measured signal.

Optionally, the device 300 shown in FIG. 3 comprises at least one inertial sensor 312. The at least one inertial sensor 312 is arranged to measure at least one item of inertial data relating to the body 304, said inertial data being used by the processing unit 308 to adjust the orientation of the visual model. In a variant, the inertial sensor 312 may be in contact with the body 304.

Optionally, the measurement sensor 306 shown in FIG. 3 carrying out the measurement of the measured signal comprises at least one near field sensor. The measurement sensor 306 is not in contact with the body 304. In the case of FIG. 3, the measurement sensor 306 measuring said measured signal comprises inductive sensors.

Each inductive measurement sensor 306 may comprise at least one coil (not shown). The signal measured at the output of each measurement sensor 306 is a voltage induced on the at least one coil of said measurement sensor 306. The measurement sensor 306 is a position sensor. In particular, the measurement sensor 306 may comprise a proximity sensor 306, preferably detecting conductive materials, for example the metal. The measurement sensor 306 thus makes it possible to detect the position of the implant 302 or areas of the implant 302. In particular, and in the case shown in FIG. 3, the measurement sensor 306 makes it possible to detect the position of the two parts 302*a* and 302*b* of the implant 302 and of the intermediate layer 303.

Each capture site of the measurement sensor 306 is arranged to provide a voltage.

Each part 302*a*, 302*b* of the implant 302 comprises at least one electronic device 314. Each electronic device 314 shown in FIG. 3 comprises at least one radio tag (not shown), said radio tag comprising an antenna (not shown) associated with an electronic chip (not shown) containing an item of implant identification data. In the case shown in FIG. 3, each electronic device 314 comprises an item of implant identification data. The implant identification data comprises at least one identifier of the implant 302, in this case that of the part 302*a* or 302*b*. Optionally, the electronic chip may comprise complementary data. The electronic chip may also comprise a storage means for storing the identifier, and optionally, the complementary data. The complementary data may comprise sensor data if the implant 302 comprises at least one sensor, for example a pressure sensor, temperature sensor, etc.

The device 300 comprises at least one electronic reader 316 arranged to exchange data with the electronic devices 314 positioned respectively in the parts 302*a* and 302*b* of the implant 302. In particular, the electronic reader 316 is arranged to read the implant identification data stored in each electronic device 314 in order to retrieve the visual model of each part 302*a* and 302*b* of the implant 302. The implant identification data of each part of the implant 302 comprises at least the identifier and/or the number of the part 302*a*, or 302*b* of the implant 302. This communication is done wirelessly.

In the case of the device 300, the visual model of the implant 302, in particular the visual model of each part of the implant, is recorded with the implant identification data on a database connected to the processing unit 308. Launching a search on this database by entering the implant identification data read by the electronic reader 316 therefore makes it possible to retrieve the visual model of each part 302*a*, 302*b* of the implant 302. Data regarding the intermediate layers 303 can also be recorded with the visual model of each part of the implant 302. The complete visual model of the implant 302 can therefore be obtained, for example by assembling the visual models of each part 302*a*, 302*b* of the implant 302. The visual model of the implant 302 can then be communicated to the processing unit 308 by a step of exchanging data between said database and said processing unit 308 in order to perform the step of providing 108 the measured image 310.

The other complementary data recorded in each electronic device 314 can also be exchanged.

The radio tag of each electronic device 314 may be a passive RFID.

The electronic reader 316 shown in FIG. 3 is connected and arranged outside the processing unit 308. Of course, in variants not shown, the electronic reader 316 can be positioned with the processing unit 308 in the same assembly (that is the same housing).

In one variant, the device 100 comprises at least one recording means arranged to acquire the at least one measured signal over time. Thus, multiple measured images 310 can be acquired over time, which makes it possible to generate a video sequence. Three-dimensional or two-dimensional dynamic imaging of the implant 302 or of each part 302*a*, 302*b* of the implant 302 can be obtained, which can make it possible to generate a video of the movement of the implant 302. The image sequence obtained can therefore be a sequence of images imaging the implant 302 in its entirety or distinct parts of the implant 302.

It is therefore possible to model the movement of the implant 302 and also the space between the two parts 302*a* and 302*b* of the implant 302 in order to verify the kinetic functioning of the implant 302. In the event of a malfunction, this modeling can, for example, compute the volume and the shape of the intermediate layer 303 which would be likely to improve the kinetics of the implant 302. This intermediate layer 303 can therefore be custom-made.

Figure 4:
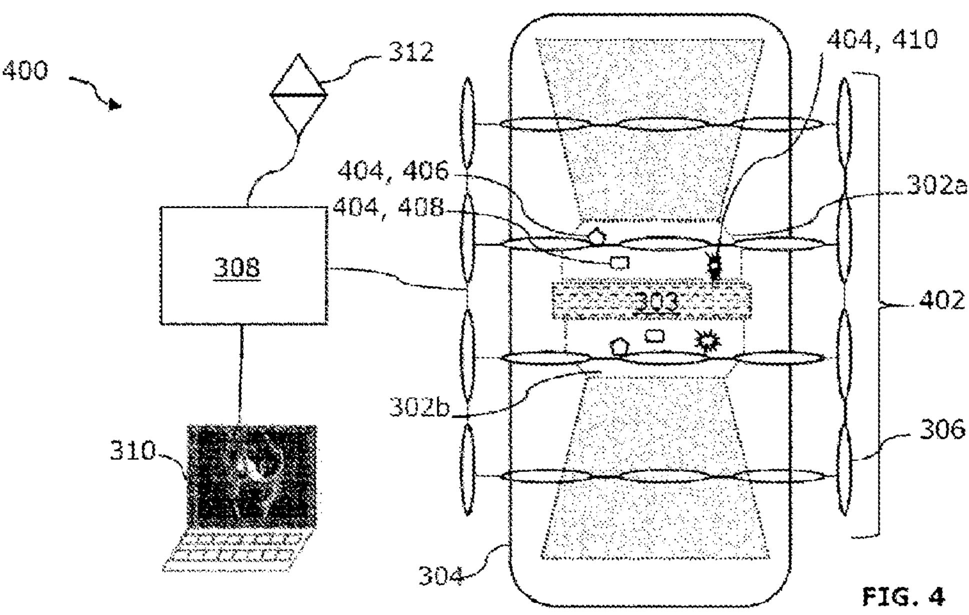
FIG. 4 is a schematic representation of a second non-limiting example embodiment of a device according to the invention.

FIG. 4 is a schematic depiction of a second example embodiment of a device 400 according to the invention.

The device 400 is an imaging device 400 of an implant 302 implanted in a body 304, arranged to implement, in a non-limiting manner, the imaging method 100 or 200 shown in FIGS. 1 and 2. Only the differences with the device 300 shown in FIG. 2 will be shown.

The device 400 shown in FIG. 4 comprises all the elements of the device 300 shown in FIG. 3, aside from the electronic devices 314 described in FIG. 3.

The device 400 comprises a plurality of measurement sensors 306 forming an array 402 of measurement sensors 306. The array 402 of measurement sensors 306 is arranged to surround the part of the body 304 comprising the implant 302.

The signals measured at the output of the measurement sensors 306 comprise a voltage.

As a non-limiting example, the array 402 comprises eight columns of seven inductive-type measurement sensors 306 arranged in a circular pattern around the implant 302. The measurement sensors 306 are all similar and are each in the form of a concentric planar loop whose dimensions are 25 millimeters by 15 millimeters. The measurement of the self inductance of each of the measurement sensors 306 of the array 402 makes it possible to obtain a map (that is, an array) formed of eight times seven cells or pixels and wherein each cell or pixel carries the inductance information necessary to provide the measured image 310. Thus, the more the array 402 comprises measurement sensors 306, the greater the resolution obtained. The inductance values vary depending on the geometry of the implant 302. As a non-limiting example, the map may be in the form of a color-level-coded array.

The at least one item of data relating to the positioning of the implant 302 is determined from the measured map combined with a supervised neural network method or a correlation method or a chart.

Furthermore, in the case shown in FIG. 4, the implant 302 does not comprise an electronic device 314. Therefore, the visual model is retrieved from a database that may be stored on a local server connected to the processing unit 308. As a non-limiting example, the visual model can be retrieved from the patient's medical records stored on the local network to which the processing unit 308 is connected.

Each part of the implant 302 shown in FIG. 4 comprises at least one location indicator 404. In the case of FIG. 4, each part of the implant 302 comprises a plurality of geographical indicators 404. Each location indicator 404 is arranged to give at least one spatial reference point of said implant and/or of parts of the corresponding implant 302. The location indicators 404 of the implant 302 have a known position and also return known signals. Thus, the signal measured at the position of this localization indicator 404 will have a clean form, which will make it possible to position a part of the implant 302 in the space and/or to determine the orientation of this part of the implant 302 from the map obtained.

In the case shown in FIG. 4, each implant 302 comprises three different types of location indicators 404.

A first type of location indicator 404 is a notch 406 or a protrusion 406 in the implant 302. This indicator comprises a particular shape so as to facilitate the recognition of this reference point. The shape of the notch can vary: square, circular, rectangular, triangular, pentagonal, star, potato-shaped, etc.

A second type of location indicator 404 is an insert 408 composed of a material different from the implant 302 in order to generate a significant contrast during the generating of the map constructed from the measurement sensors 306.

A third type of location indicator 404 is an LC resonator 410, affixed to the implant 302 and arranged to amplify a magnetic and/or electric field re-emitted toward the measurement sensors 306 so as to create a hot spot on the map.

In the device 400, the visual model is stored in a database, consequently the device 400 is arranged to perform a step of the method 100 or 200 for exchanging data between said processing unit 308 and said database to perform the step of provision 108. Of course, in this case, the method according to the invention may optionally comprise searching a database for the visual model based on the implant identification data (that is, identifier of the implant 302).

Figure 5:
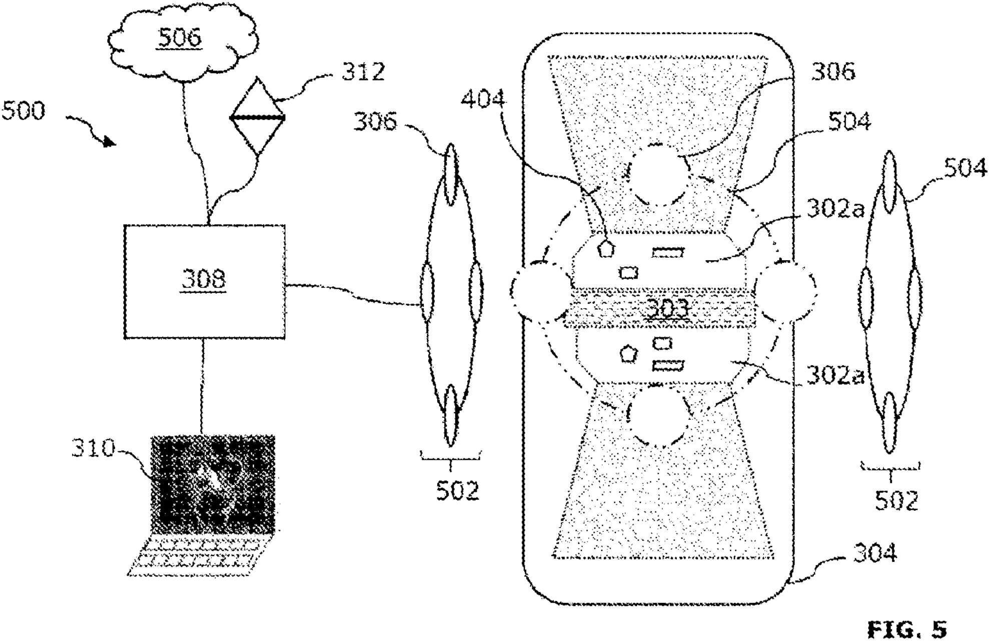
FIG. 5 is a schematic representation of a third non-limiting example embodiment of a device according to the invention.

FIG. 5 is a schematic depiction of a second example embodiment of a device 500 according to the invention.

The device 500 is an imaging device 500 of an implant 302 implanted in a body 304, arranged to implement the imaging method 100 or 200 shown in FIGS. 1 and 2. Only the differences with the device 400 shown in FIG. 4 will be described.

The device 500 shown in FIG. 5 comprises all the elements of the device 400 shown in FIG. 4.

The device 500 comprises multiple arrays 502 of measurement sensors 306. In particular, and in a non-limiting manner, the device 500 of FIG. 5 comprises three arrays 502 of measurement sensors 306 arranged to surround the body portion 304 comprising the implant 302. Each array 502 comprises a plurality of measurement sensors 306, including a measurement sensor 306 used as a transmitter and multiple measurement sensors 306 used as receivers. The measurement sensor 306 used as a transmitter is arranged to emit at least one signal intended for the implant 302, and preferably to each part 302*a*, 302*b* of the implant 302. The measurement sensors 306 used as receivers are arranged to receive at least one signal from each part 302*a*, 302*b* of the implant 302. The received signal may be a reflected signal (that is, reflection of the signal emitted by the electrical sensor 306 used as transmitter on the implant or on one or each part 302*a*, 302*b* of the implant 302) by the implant 302. The measurement sensor 306 used as a transmitter comprises an inductor (that is a coil) in the form of a loop 504. The measurement sensors 306 used as receivers are positioned on the loop 504. Each measurement sensor 306 used as a receiver on the same loop 504 is independent of the other measurement sensors 306 used as receivers on the same loop 504. The loop 504 is closed and has a circular shape. The measurement sensors 306 used as receivers each comprise an inductor. The inductor may be a coil. Each array 502 is arranged to provide a number n of measurements of the measured signal as a function of the number of measurement sensors 306 used as receivers on said loop 504. Four measurement sensors 306 used as receivers are positioned on the loop 504 of the sensor used as a transmitter. Thus, the device 500 measures three times four measured signals which, as in the device of FIG. 4, will be represented in the form of a map (that is, array) of size 3×4. In the device 500 shown in FIG. 5, the arrays 502 are similar. In a variant not shown, the arrays can be different in size (that is to say, have more or less measurement sensors 306 used as receivers and/or transmitters) and/or in shape. The processing unit 308 can utilize all of the signals or some of the measured signals.

In the case of FIG. 5 and in a non-limiting manner, the signal measured at the output of each measurement sensor 306 used as a receiver is an electrical voltage, in particular an electrical voltage induced on each measurement sensor 306 used as a receiver.

Thus, for each array 502, four mutual inductance measurements are carried out in order to obtain a higher-contrast map (that is to say of better sensitivity) than the arrangement of the sensors 306 shown in FIG. 4.

The device 500 is connected to a computer network 506 connected to the processing unit 308. The computer network 506 is itself connected to a database comprising the visual model relating to said implant. The device 500 is therefore able to communicate with an external network 506 to recover the at least the visual model in order to carry out the step of providing 108 the measured image 310. The device is also able to communicate with the external network 506 to carry out the preliminary phase 202. This communication is done via the Internet, by WIFI.

Figure 6:
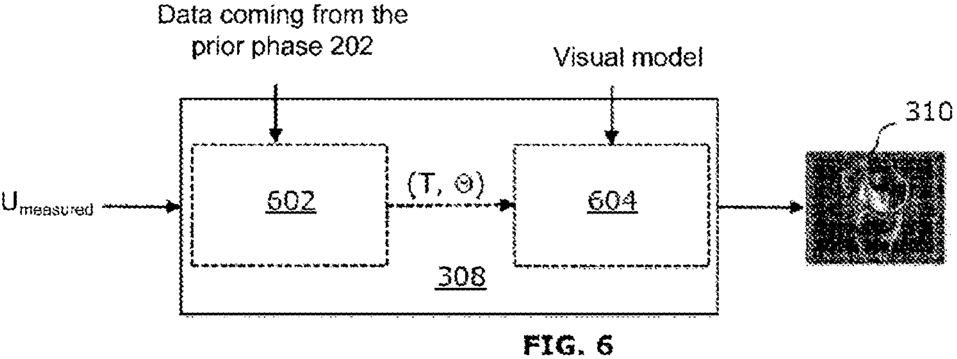
FIG. 6 is a schematic representation of a non-limiting example of the processing unit of a device according to the invention.

FIG. 6 is a schematic representation of a non-limiting example of the processing unit 308 of the device 300, 400, 500 or 600.

The processing unit comprises a first computing module 602 configured to determine the at least one item of positioning data as a function of the at least one measured signal $U_{measured}$ and the previously established model.

In a non-limiting example, the previously established model can be a supervised neural network trained with, for example, the data recorded following the preliminary phase 202.

In this case, the first computing module 602 uses the at least one measured signal, for example a voltage $U_{measured}$ provided by a measurement sensor 306. The at least one measured signal may be the inductance map.

The processing unit may comprise a second computing module 604 to provide the measured image 310 as a function of the at least one item of positioning data $\ominus$, T and of the visual model of the implant.

The at least one item of positioning data determined in the determining step 106 comprises at least one item of data relating to the position T and the orientation $\ominus$ of the implant 302, and in this case, of each part 302*a* and 302*b* of the implant 302. The at least one item of position data T and orientation data $\ominus$ are then combined with the visual model of the implant 302 (each part 302*a*, 302*b* of the implant 302 as well as that of the intermediate layer 303) to provide the measured image 310. The visual model of the implant may comprise a three-dimensional image of each part 302*a*, 302*b* of the implant 302.

The invention claimed is:

1. A method for imaging an implant implanted in a body, comprising at least one iteration of a characterization phase comprising the following steps:

measuring a positioning of the implant by at least one sensor, known as the measurement sensor, located outside the body, by supplying at least one electrical signal, known as the measured signal, relating to the implant;

determining, by a processing unit, at least one item of data relating to the positioning of the implant as a function of said measured signal and of a previously established model linking the at least one measured signal to the at least one item of data relating to positioning, said at least one item of data relating to the positioning including at least one orientation data of the implant;

providing, by a processing unit, an image, referred to as a measured image, from the at least one item of positioning data and a visual model relating to the implant; and adapting the visual model based on said at least one item of data relating to the positioning of the implant.

2. The method according to claim 1, wherein the visual model relating to the implant is a three-dimensional image of the implant, and wherein the measured image is a three-dimensional image.

3. The method according to claim 1, wherein the measuring step comprises measuring, by at least one inertial sensor, at least one item of inertial data relating to the body, and wherein the step of providing the measured image comprises an adjustment of the orientation of the visual model.

4. The method according to claim 1, comprising multiple iterations of the characterization phase each providing the measured image, the method further comprising generating a video from said measured images.

5. The method according to claim 1, further comprising an identification step to retrieve said visual model relating to the implant, said identification step comprising a step of reading, by an electronic reader, an item of identification data stored in an electronic device integrated into the implant.

6. The method according to claim 1, wherein the visual model is stored in a database, the method comprising a step of exchanging data between said processing unit and said database to perform the providing step.

7. The method according to claim 1, further comprising, prior to the first iteration of the characterization phase, a preliminary phase carried out when the implant is outside the body, said preliminary phase comprising at least one iteration of the following steps of:

measuring the implant outside of the body, by the at least one sensor known as the measurement sensor, by supplying at least one electrical signal, known as the reference signal; and storing in a database, of the at least one reference signal in association with said at least one item of positioning data, referred to as an item of reference positioning data, of the implant.

8. The method according to claim 1, wherein the previously established model comprises:

a supervised neural network trained with a database and taking as input the at least one measured signal, said database linking an electrical signal with an item of positioning data, or a pre-recorded table associating at least one electrical signal with at least one item of data relating to the positioning of said implant, or a mathematical relationship between the at least one measured signal and the at least one item of positioning data.

9. A device for imaging an implant implanted in a body, comprising means arranged to implement the imaging method according to claim 1, the device comprising:

at least one sensor, known as the measurement sensor, located outside the body and arranged to supply at least one electrical signal, known as the measured signal, relating to the implant;

a processing unit arranged to:

determine at least one item of data relating to the positioning of the implant as a function of the measured signal and of a previously established model linking the at least one measured signal to the at least item of data relating to positioning; and provide an image, referred to as the measured image, from at least one item of positioning data and a visual model relating to the implant.

10. The device according to claim 9, comprising at least one inertial sensor arranged to measure at least one item of inertial data relating to the body, said inertial data being used by the processing unit to adjust the orientation of the visual model.

11. The device according to claim 9, wherein at least one measurement sensor performing the measurement of said measured signal comprises at least one near field sensor.

12. The device according to claim 9, comprising multiple measurement sensors forming an array of sensors, said array being arranged to surround at least part of the body comprising the implant.

13. The device according to claim 9, comprising multiple measurement sensors forming a plurality of arrays of measurement sensors arranged to surround a part of the body comprising the implant, each array comprising:

a measurement sensor used as a transmitter; and a plurality of measurement sensors used as receivers and positioned on the measurement sensor used as a transmitter.

14. The device according to claim 9, wherein at least one measurement sensor measuring said measured signal comprises:

at least one capacitive sensor, and/or at least one inductive sensor.

15. The device according to claim 9, comprising at least one electronic reader arranged to read an item of identification data stored in an electronic device integrated into the implant to retrieve said visual model relating to the implant.

* * * * *